(12) United States Patent
Leitner

(10) Patent No.: US 7,780,677 B2
(45) Date of Patent: Aug. 24, 2010

(54) METHOD OF DETERMINING THE POSITION OF THE ARTICULAR POINT OF A JOINT

(75) Inventor: Francois Leitner, Uriage (FR)

(73) Assignee: Aesculap AG, Tuttlingen (DE)

( * ) Notice: Subject to any disclaimer, the term of this patent is extended or adjusted under 35 U.S.C. 154(b) by 1038 days.

(21) Appl. No.: 11/507,158

(22) Filed: Aug. 21, 2006

(65) Prior Publication Data

US 2006/0282023 A1    Dec. 14, 2006

Related U.S. Application Data

(62) Division of application No. 10/308,622, filed on Dec. 3, 2002, now Pat. No. 7,209,776.

(51) Int. Cl.
| | |
|---|---|
| *A61B 17/58* | (2006.01) |
| *A61B 17/60* | (2006.01) |
| *A61B 5/103* | (2006.01) |
| *A61B 5/117* | (2006.01) |
| *A61F 2/00* | (2006.01) |

(52) U.S. Cl. .................. 606/102; 606/86 R; 606/88; 606/53; 600/595; 600/587

(58) Field of Classification Search .............. 600/595, 600/587; 128/898, 897, 920; 623/39, 914; 606/53, 88, 86 R See application file for complete search history.

(56) References Cited

U.S. PATENT DOCUMENTS

| 4,631,676 A | 12/1986 | Pugh ........................... 600/595 |
| 5,249,581 A | 10/1993 | Horbal et al. ................ 128/664 |
| 5,564,437 A | 10/1996 | Bainville et al. ............. 128/774 |
| 5,611,353 A | 3/1997 | Dance et al. ................. 128/782 |
| 5,682,886 A | 11/1997 | Delp et al. ................... 128/653.1 |
| 5,871,018 A | 2/1999 | Delp et al. ................... 128/898 |
| 5,880,976 A | 3/1999 | DiGioia III et al. .......... 364/578 |
| 5,961,474 A | 10/1999 | Reis ............................ 600/595 |
| 5,995,738 A | 11/1999 | DiGioia, III et al. ..... 395/500.32 |
| 6,002,859 A | 12/1999 | DiGioia, III et al. ..... 395/500.32 |
| 6,162,190 A | 12/2000 | Kramer ....................... 600/595 |
| 6,385,475 B1 | 5/2002 | Cinquin et al. .............. 600/407 |
| 6,877,239 B2 | 4/2005 | Leitner et al. ................ 33/512 |
| 6,915,150 B2 | 7/2005 | Cinquin et al. .............. 600/407 |
| 6,947,783 B2 | 9/2005 | Immerz ....................... 600/410 |

(Continued)

FOREIGN PATENT DOCUMENTS

DE    19632273    2/1998

(Continued)

*Primary Examiner*—Max Hindenburg
*Assistant Examiner*—H. Q. Nguyen
(74) *Attorney, Agent, or Firm*—RatnerPrestia

(57) ABSTRACT

A non-invasive method for determining the articular point of a knee joint is disclosed. The method uses a surgical navigation system having stereoscopic cameras which track the positions of infrared emitting or reflecting markers attached to leg portions on either side of the knee joint. A movable marker is used to palpate known landmarks on the leg portions to determine their positions. The leg portions are moved to determine the trajectories of the landmarks relative to the joint. Positional information from the cameras is fed to a data processing system with resident software which uses the positional information and trajectories to mathematically determine the positions of the knee joint articular point according to the laws of kinematics.

4 Claims, 5 Drawing Sheets

U.S. PATENT DOCUMENTS 7,033,360 B2 * 4/2006 Cinquin et al. ............ 606/86 R
7,611,519 B2 * 11/2009 Lefevre et al. .............. 606/102

FOREIGN PATENT DOCUMENTS

| EP | 01/12141 | 10/2001 |
| WO | WO 94/01042 | 1/1994 |
| WO | WO 00/48507 | 8/2000 |

* cited by examiner

METHOD OF DETERMINING THE POSITION OF THE ARTICULAR POINT OF A JOINT

CROSS REFERENCE TO RELATED APPLICATION

This application is a divisional of U.S. application Ser. No. 10/308,622, filed Dec. 3, 2002.

FIELD OF THE INVENTION

The invention concerns a method for the pre-operative determination of the position of the articular point of a joint and specifically a knee joint.

BACKGROUND OF THE INVENTION

Successful orthopaedic surgery, for example, the replacement of hip and knee joints with endoprostheses, the correction of knee deformities such as genu valgum (knock knee) and genu varum (bowleg) by osteotomy requires precise knowledge of the position of the articular point of the joint being operated on. The articular point represents an imaginary joint center about which the bones connected at the joint rotate. More precision in the knowledge of the articular point of a joint results in longer lasting replacement joints and more effective correction of deformities.

To improve orthopaedic surgery, navigation systems have been developed, such as disclosed in U.S. Pat. No. 6,385,475 to Cinquin et al and hereby incorporated by reference. Such systems use markers attached to bones on opposite sides of the joint connecting the bones. The markers are observable by a stereoscopic camera system connected to a data processing system such as a computer that can record the positions of the markers in space and, using software, calculate the kinematic motion of the bones, as well as other mathematical parameters and relationships. The markers attached to the bones establish a coordinate reference system relative to each bone. Additional camera observable markers are freely moveable and may be used to palpate (touch) specific landmarks on the bones in order to ascertain the position of the landmarks in the coordinate reference systems of the bones. The positions of such landmarks are used by the data processing system software, along with the relative motion of the bones connected at the joint of interest, to calculate the geometric and kinematic relationships needed to guide the orthopaedic surgery. Included among these parameters are articular points or joint centers.

Present methods for determining the position of articular points, such as the knee center, require that the knee joint be surgically opened to provide access to the anatomical center of the knee (a landmark point on the femur) so that this point may be palpated by a movable marker to establish its precise location in space relative to the femur coordinate reference system defined by the marker attached to the femur. Using the location of the anatomical knee center in conjunction with the positions of other landmarks (such as the medial and lateral epicondyles, also determined by palpation), as well as motion of the tibia relative to the femur, the data processing system software can calculate a relatively accurate position of the knee center in the femur and tibia coordinate systems. The position of the knee center is then used to provide further information directing the placement of endoprostheses or guiding the bone cutting in an osteotomy.

Methods involving surgically opening the knee joint to determine the position of the knee center are acceptable when the contemplated operation also requires access to the knee joint, such as during a total knee arthroplasty (knee replacement). However, for less invasive procedures, such as the mere gathering of information for pre-operative diagnostic purposes, or an osteotomy to correct a knee deformity, that do not require the knee be surgically opened, it is not advantageous to open the knee merely to palpate the anatomical center to ascertain the knee center location. Clearly, there is a need for a non-invasive method for determining the position of the knee center, as well as the articular points of other joints.

SUMMARY AND OBJECTS OF THE INVENTION

The invention concerns a method for determining the position of an articular point of a central joint between two substantially rigid bodies, the central joint being located between first and second outer joints located at the ends of the first and second rigid bodies distal to the central joint. The steps of the method include identifying the position of a first point on the first rigid body located substantially at the central joint. Next, the position of a first articular point of the first rigid body at the first outer joint is determined. A first axis between the first articular point and the first point previously determined is defined. Then the respective positions of a second and a third point on the first rigid body on opposite sides of the central joint are identified. A plane, substantially perpendicular to the first axis and at substantially equal respective rectangular distances to the second and third points is defined. The intersection of the plane and the first axis is used as an initial estimate of the articular point of the central joint. Next the position of a second articular point of the second rigid body at the second outer joint is determined. A region in the plane having a predetermined size is identified, the region including the initial estimate of the articular point of the central joint as well as other points. The second articular point is then moved relatively to the first rigid body by rotating the second rigid body about the central joint. A multiplicity of different positions of the second articular point are identified during the rotation of the second rigid body. One point among a multiplicity of points within the region is identified for which the position is substantially invariant for each of the positions of the second articular point, the one point being the articular point of the central joint.

The method according to the invention is specifically applicable to determining the position of the articular point of the knee joint (the knee center) between the femur and the tibia. Important landmarks on the knee joint for determining the articular point position include the patella (knee cap) and the medial and lateral epicondyles (the eminences of the femur above the knee joint). The method of determining the position of the knee articular point according to the invention comprises identifying the position of the patella and determining the position of the articular point of the femur at the hip joint. This information is then used to define a femoral axis that extends between the femur articular point and the patella. Next, the positions of the medial and lateral epicondyles are identified. A plane is defined that is substantially perpendicular to the femoral axis and at substantially equal respective rectangular distances to the positions of the medial and lateral epicondyles. The intersection of the plane and the femoral axis is the initial estimate of the articular point of the knee joint.

Following these steps, a region in the plane having a predetermined size is defined. The region includes the initial estimate of the articular point position of the knee joint and is preferably a circle centered on this point. The position of an articular point of the tibia at the ankle joint is then defined and this point is moved relatively to the femur by rotating the tibia about the knee joint while recording multiple positions of the tibia articular point during the rotation. The one point within the aforementioned region containing the knee articular point is identified as the knee articular point whose position is substantially invariant for each of the positions of the tibia articular point.

Preferably, the substantially invariant point is defined by a point within the region having the smallest standard deviation of distance between that point and the tibia articular point for all of the recorded positions of the tibia articular point.

Preferably, the step of determining the position of the femur articular point comprises the steps of moving the patella by rotating the femur about the hip joint, identifying a plurality of positions of the patella during the motion of the patella about the hip joint and then determining mathematically a common point at the hip joint having substantially the same distance to all of the positions of the patella. The common point is the femur articular point.

Preferably, the step of determining the position of the tibia articular point at the ankle comprises the steps of identifying the respective positions of medial and lateral malleoli (protuberances) on opposite sides of the ankle joint and the position of an anterior point of the ankle located in the sagittal plane of the tibia. Using this positional information, a first line between the medial and lateral malleoli is defined and a second line is projected from the anterior point to perpendicularly intersect the first line at an intersection point. The tibia articular point is determined as the intersection point of these two lines.

It is an object of the invention to provide a method for determining the articular point or center of a joint.

It is another object of the invention to provide a non-invasive method for determining the articular point of a joint.

It is yet another object of the invention to provide a method of determining the articular point of a joint that does not require surgically opening the joint.

It is still another object of the invention to provide a method of determining the articular point of a joint based upon the kinematics of the joint and landmarks whose location may be identified by palpation techniques.

It is again another object of the invention to provide a method of determining the articular point of a joint to provide information for performing an osteotomy affecting the joint.

These and other objects and advantages will become apparent upon consideration of the drawings and detailed description of the preferred embodiments of the invention.

DETAILED DESCRIPTION OF THE EMBODIMENTS

Figure 1:
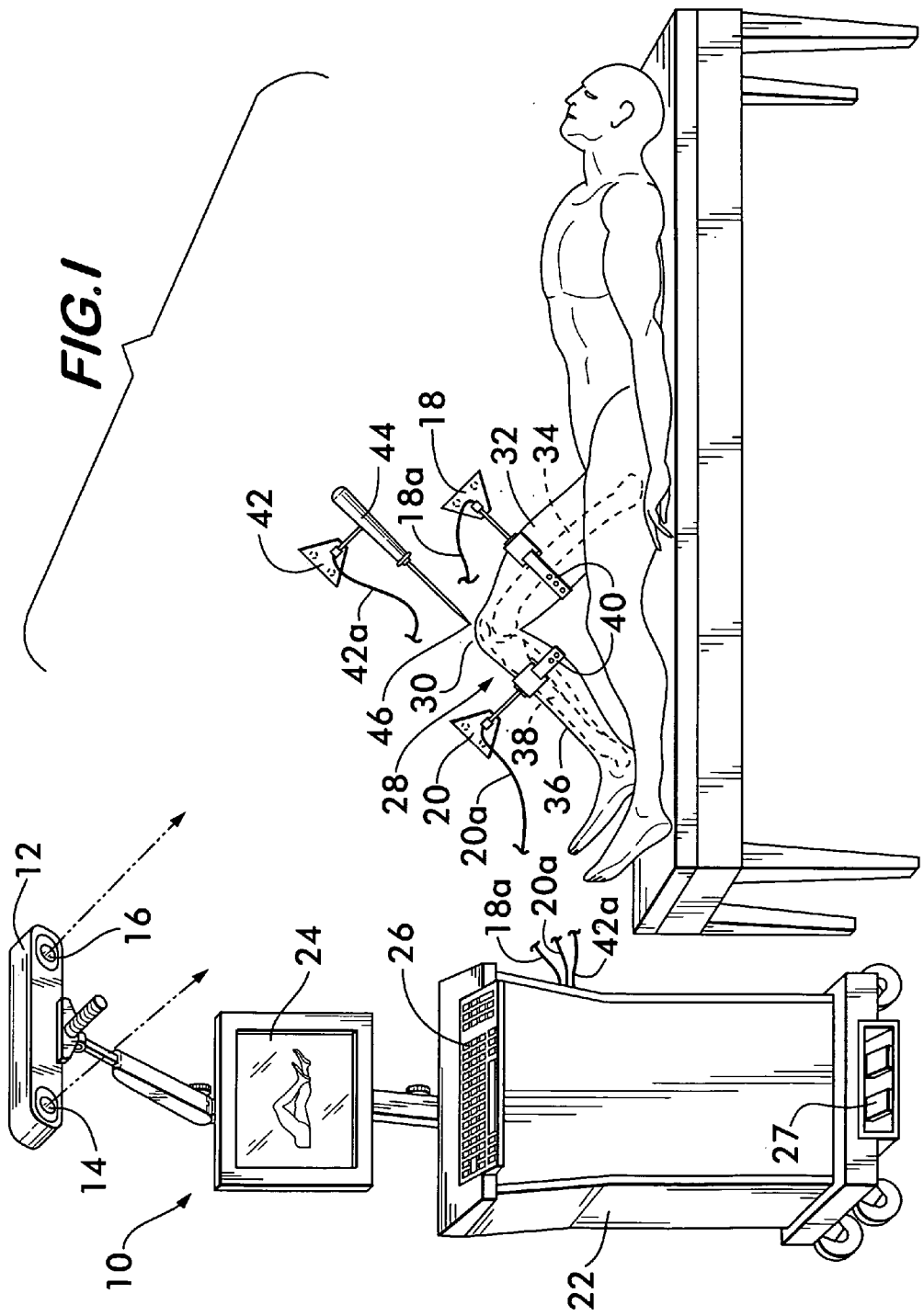
FIG. 1 is a perspective view of an apparatus used to perform the method of joint articular point determination according to the invention.

FIG. 1 illustrates a type of orthopaedic surgical navigation device 10 preferably used to execute the steps of the method of determining the position of the knee articular point according to the invention, it being understood that the method is not limited to any particular device or any particular joint.

Navigation device 10 comprises a stereoscopic sensor system 12 having sensors such as cameras 14 and 16 separated from one another so as to view markers 18 and 20 from different locations, thus allowing the positions of the markers in space to be deduced by techniques such as triangulation based upon comparison of the arrival times of signals from the markers at the different cameras. The cameras 14 and 16 are sensitive to infrared radiation so as to be usable in ambient visible light.

The cameras 14 and 16 generate signals describing the detected positions of markers 18 and 20, the signals being fed to a data processing system 22, preferably comprising a microprocessor with resident software. The software is written to understand the camera signals and identify the positions of the markers which can then be stored and mathematically manipulated as needed to calculate or deduce further information. Information from the software is communicated to a user of the system by means of a computer monitor 24, and the user communicates with the software by means of a keyboard 26 and foot pedals 27.

Markers 18 and 20 are attachable to the leg 28 of a patient on each side of the knee joint 30, the articular point of which is to be determined. One marker, 18, is attached to the upper leg portion 32 which includes the femur 34, the other marker, 20, is attached to the lower leg portion 36 which includes the tibia 38. The markers are preferably attached by means of respective harnesses 40 that prevent each marker from shifting in position on the leg once attached. Harnesses 40 allow the markers to be attached without the use of invasive surgery, thus fulfilling one of the objects of the invention. The markers may also be attached directly to the femur and tibia using bone screws if the bone is surgically exposed. It is important that the markers be securely attached to the leg portions so that they always indicate the true locations of the leg portions and not a shift in the marker location relative to the leg. This ensures that any calculations based upon the locations of the markers will be meaningful with respect to the actual leg locations.

A movable marker 42 is not attached to any part of the leg but is variably positionable at any point along the leg. Marker 42 is attached to a pointer 44, having a tip 46. The position of the tip 46 relative to the marker 42 is known to the software so that positioning the tip 46 at a landmark on the leg 28 (known as "palpating" the landmark) allows the software to precisely identify the position of the landmark relative to the position of the fixed markers 18 and 20. Such relative positional information is useful for calculating parameters needed to determine the position of the knee articular point as described below.

Markers 18, 20 and 42 emit infrared radiation visible to the cameras 14 and 16 allowing them to see and track the relative positions and motions of the bodies to which the markers 18 and 20 are attached or that marker 42 is palpating. The markers may have active emitters that generate their own infrared radiation, or passive emitters that reflect infrared radiation from an infrared radiation source associated with the navigation device 10.

Figure 3:
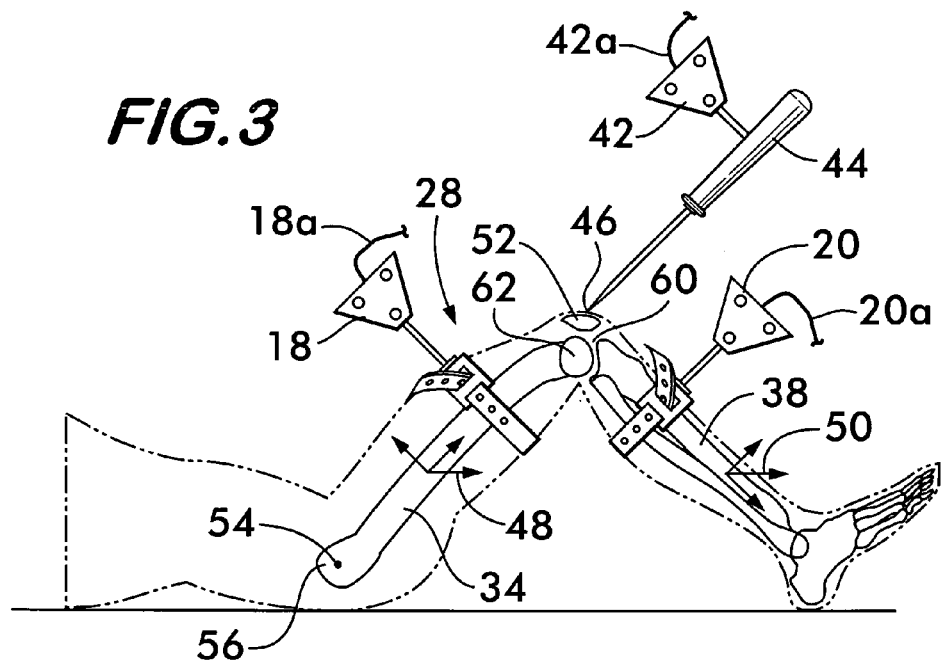
FIGS. 3-7 are elevational views of a leg showing the skeletal structure and illustrating various steps of the method according to the invention.

In the method according to the invention, the locations of the markers 18 and 20 are identified to the software of the data processing system 22 by the sensor system 12. As shown in FIG. 3, the marker locations establish frames of reference 48 and 50 on the femur 34 and tibia 38 respectively. The locations of landmarks on the leg 28 as well as the relative motion of the landmarks and the relative motion of the femur and tibia may be identified within the frames of reference.

Method Description

A method of determining the position of the articular point of the knee joint (also called the "knee center") is described below. The method is not limited to the knee joint but may be used on any joint connecting two rigid bodies.

With reference to FIG. 1, the method according to the invention first requires that marker 18 be attached to the upper leg portion 32 which includes the femur 34. Marker 20 is attached to lower leg portion 36 which includes the tibia 38. Once securely attached by means of harnesses 40, markers 18 and 20 are viewed by cameras 14 and 16 and defined to the software of the data processing system 22 as being attached to the femur and tibia respectively. For the active emitting markers illustrated, the software controls the infrared emissions from each marker via communication cables 18a, 20a and 42a associated with each marker. Thus the software can distinguish between the markers by turning them on one at a time. It is preferred to dedicate one marker, for example 18, to always be placed on the upper leg portion 32, another marker, 20, to always be placed on the lower leg portion 36, and the third marker, 42, to be the movable marker. This allocation of markers is programmed into the software, and when the markers are visible to the cameras 14 and 16 the software will know which marker is on which leg portion. Foot pedals 27 may be used to communicate interactively in response to the software to indicate that the markers are in place. With the markers 18 and 20 in position as shown in FIG. 1, foot pedal 27 is pressed in response to a prompting command from the software displayed on the monitor 24 to indicate that the markers are in position and ready. The software then activates the markers 18 and 20 which emit infrared signals that are read by the cameras 14 and 16. The cameras identify the marker locations in space and transmit the information to the software which records their location and mathematically establishes coordinate reference frames 48 and 50 shown in FIG. 3 for the femur and the tibia.

Next, as shown in FIG. 3, the position of the patella 52 (knee cap) is identified by palpating (touching) the patella with the tip 46 of pointer 44. During palpation, the movable marker 42 attached to pointer 44 is viewed by the cameras 14 and 16 and the position of the patella 52 is identified to the software and thus known relative to both the femur and tibia reference frames 48 and 50. Marker 42 may be identified to the software interactively by holding the pointer 44 stationary with its tip 46 on the patella 52 and marker 42 visible to the cameras 14 and 16 and then pressing the foot pedal 27 in response to a prompting command requesting input of the patella location, the command being visible on the monitor 24. Using the communication cables 18a, 20a and 42a, the software activates the markers 18, 20 and 42 in sequence, their infrared emissions are viewed by the cameras 14 and 16 and the software is able to distinguish between the three markers and identify and record their relative locations upon receipt of the information from the cameras.

Figure 4:
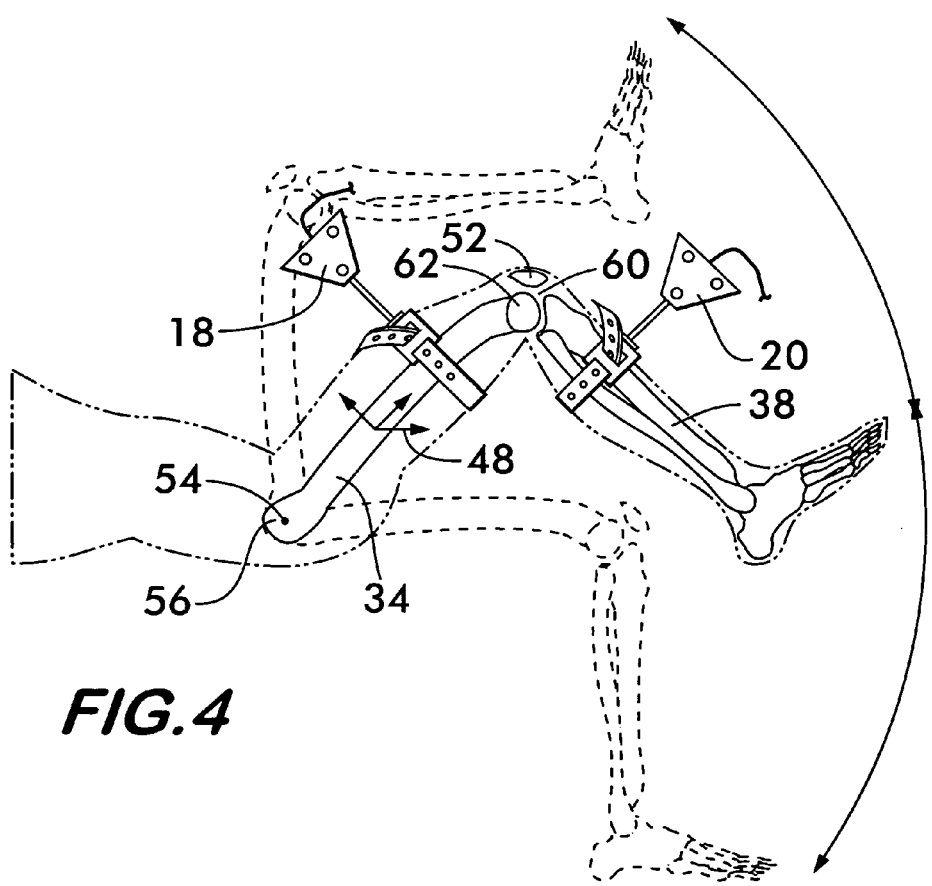

Knowing the position of the patella 52 in the femur reference frame 48, the femur articular point 54 may be determined by moving the femur 34 about the hip joint 56 as illustrated in dashed line in FIG. 4 in response to a prompting command on the monitor 24. Cameras 14 and 16 observe the motion of marker 18 and signal a number of discrete positions of the marker to the software. The software calculates the positions of the patella 52 from the positions of marker 18 observed by the cameras during the femur motion. Particularly since the patella 52 is at the end of a rigid body (the femur 34) whose opposite end is constrained in its motion by a ball joint (the hip joint 56), the software knows that the positions the patella may take all lie on a sphere centered at the articular point of the hip joint. Thus, from the marker positions observed and identified to the software during the motion of the femur and the known spatial relationships of the palpated patella 52 relative to the femoral marker 18, the software can calculate the femur articular point 54 in the femur reference frame 48, the articular point 54 being a common point at the hip joint that has substantially the same distance to all of the positions of the patella 52.

Knowing the position of the femur articular point 54, the femoral axis 58 can be defined. As shown schematically in FIG. 2, the femoral axis 58 is an imaginary line extending between the femur articular point 54 (i.e., the center of the hip joint) and the position of the patella 52 and is defined mathematically by the software. The femoral axis 58 does not necessarily coincide with the femur 34 and is used in conjunction with the positions of the medial and lateral epicondyles 60 and 62 respectively, to determine an initial estimate of the knee articular point as described below. The epicondyles are eminences that protrude from either side of the femur 34 above the knee joint 30.

Figure 2:
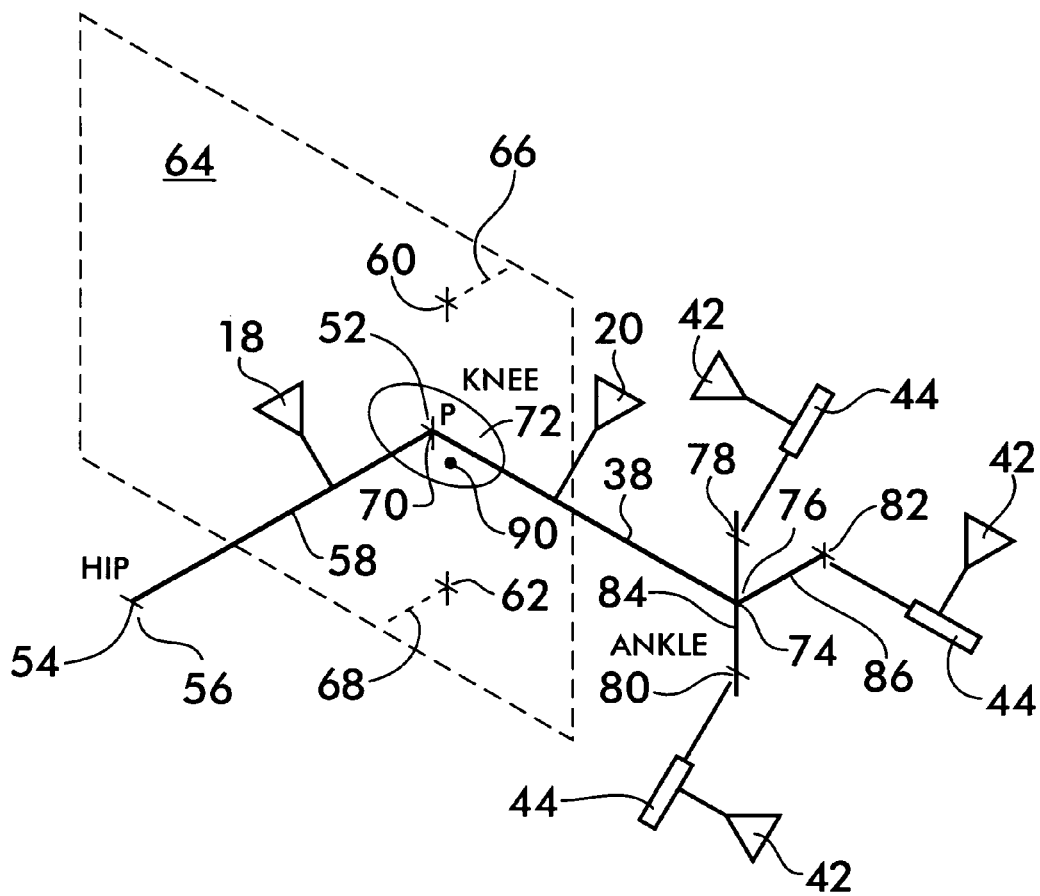
FIG. 2 is a schematic diagram illustrating various landmarks, bones and mathematical constructs important to determining the knee articular point by the method according to the invention.
Figure 5:
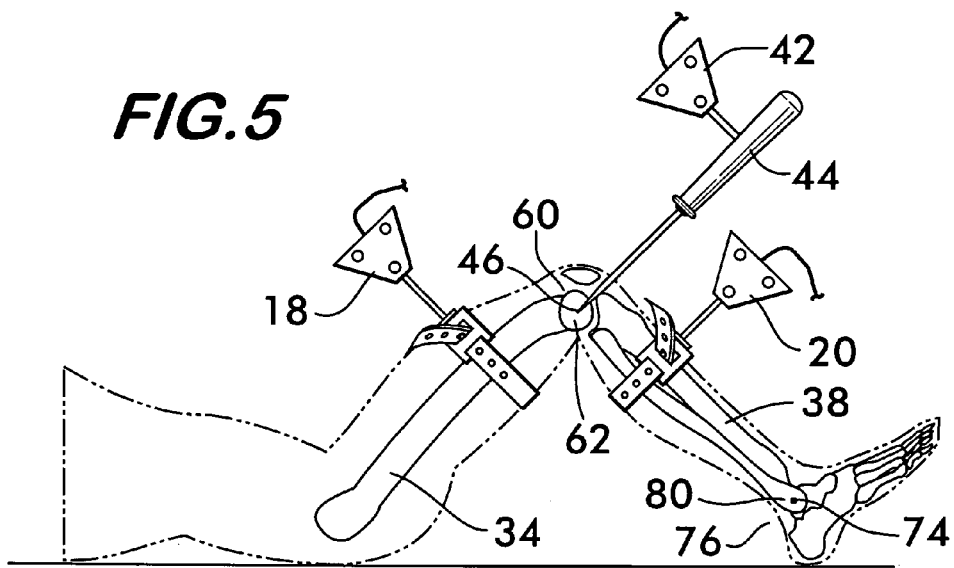

As shown in FIG. 5, the positions of the medial and lateral epicondyles 60 and 62 respectively are identified by palpating each with the tip 46 of pointer 44 and allowing the movable marker 42 to be observed by the cameras 14 and 16. As each epicondyle is palpated, its respective position is identified to the software, again conveniently by responding to interactive prompts on the monitor 24, the user positioning the pointer 44 appropriately in response to a command and pressing the pedal 27. Next, as illustrated in FIG. 2, the software mathematically defines a plane 64 perpendicular to the femoral axis 58. The plane 64 is located along the femoral axis where the plane is at substantially equal respective rectangular distances 66 and 68 to the positions of the medial and lateral epicondyles 60 and 62. The point of intersection 70 between the plane 64 and the femoral axis 58 is the initial estimate of the knee articular point. Once the initial estimate point 70 is established, a region 72 in the plane 64 is defined that includes the estimate point. Preferably, the region 72 is a circle of 1 cm diameter centered on the initial estimate point 70. Region 72 contains candidate points for the knee articular point, one of which will be selected mathematically, preferably using statistical methods as described below.

Figure 6:
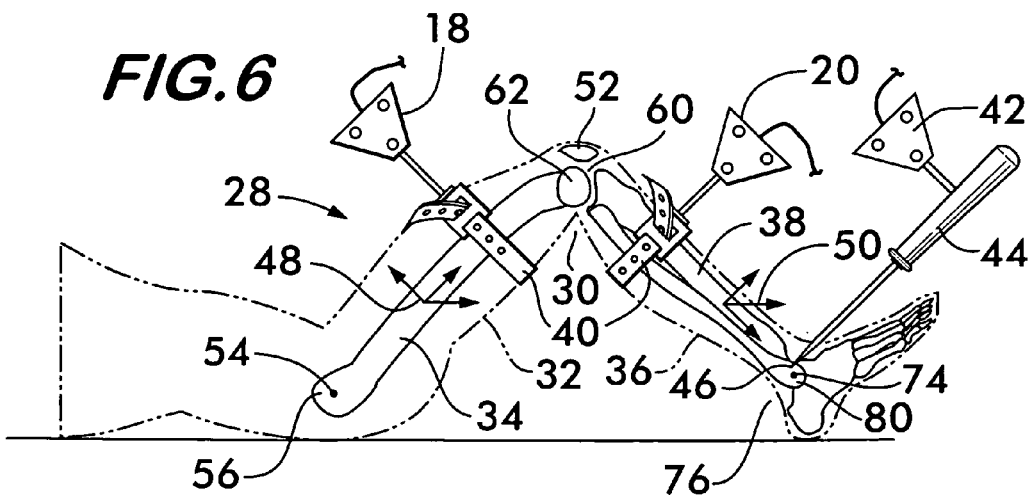

Next, as shown in FIGS. 2 and 6, the position of the articular point 74 of the tibia at the ankle joint 76 is determined with respect to the fixed marker 20, preferably using the positions of the medial and lateral malleoli 78 and 80. The malleoli are the protuberances on either side of the ankle joint. The positions of the medial and lateral malleoli 78 and 80 respectively are identified by palpating them with the tip 46 of the pointer 44 attached to the movable marker 42 when prompted by the software. During respective palpation, the marker 42 is observed by the cameras 14 and 16 which signals the respective positional information of the malleoli to the software. Actuation of foot pedal 27 may be used to effect data capture as with previous palpations. Next, the position of an anterior point 82 of the ankle joint 76 is identified by palpating the anterior region of the ankle in the sagittal plane of the tibia 38. Knowing the positions of the malleoli 78 and 80, the software mathematically defines an imaginary line 84 (see FIG. 2) between the medial and lateral malleoli 78 and 80. Knowing the position of anterior point 82, the software then mathematically projects another line 86 from the anterior point 82 that intersects line 84 substantially perpendicularly. The point 74 where lines 84 and 86 intersect is defined as the tibia articular point.

Figure 7:
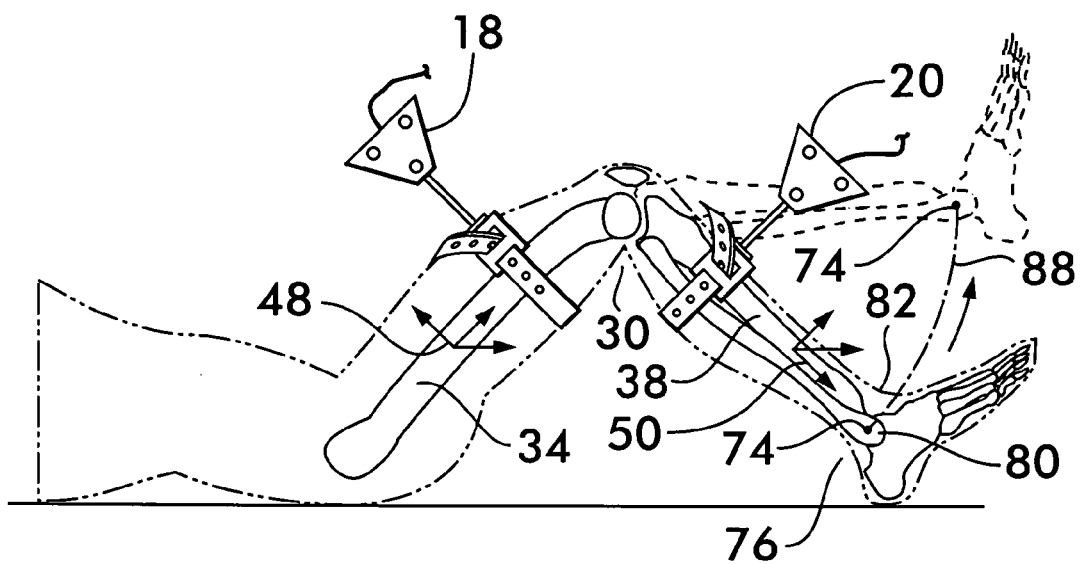

As shown in FIG. 7, the tibia 38 is next rotated about the knee joint 30 through a specified range of motion. Preferably, the tibia 38 is initially placed at a substantially right angle to the femur 34 and then rotated in flexure (away from the femur), as shown in dashed line, through an angle between about 10° and about 90°, but preferably between about 10° and about 40°. Moving the tibia moves the tibia articular point 74 through a trajectory 88 relative to the knee joint 30, the motion being constrained by the nature of the knee joint, which may be approximated as a hinge for angular motion between about 10° and about 40°, and the fact that the articular point is at the end of a rigid body (the tibia 38) movable about the hinge joint (the knee 30). Cameras 14 and 16 observe the motion of marker 20 on the tibia 38 relative to the marker 18 on the femur 34 and signal the positions of a multiplicity of points of the marker 20 to the software. The software knows the position of the tibia articular point 74 in the tibia reference frame 50 (i.e., relatively to the marker 20) for all motions of the tibia. Using this information, the software can calculate the corresponding motion of the articular point 74 relative to the points within the region 72 (fixed in the femur reference frame 48 as shown in FIG. 2) through the trajectory 88 defined by the constraints of a rigid body (the tibia 38) rotating about a hinge joint (the knee joint 30) relative to another rigid body (the femur 34). The software then uses the positional information of the tibia articular point 74 during its motion through trajectory 88 to choose a point from among the points in the region 72 (see FIG. 2) which represents the best estimate of the position of the knee articular point 90 based upon a particular set of criteria.

Preferably, the point within region 72 having a position that is substantially invariant for a multiplicity of positions of the tibia articular point along its trajectory 88 about the knee joint 30 is selected as the knee center or knee articular point 90. For example, the point in region 72 that has the smallest standard deviation of distance to the tibia articular point 74 for a multiplicity of positions of the tibia articular point 74 along the trajectory 88 may be selected as the knee articular point or knee center 90. The accuracy with which the position of the knee articular point 90 is determined will be proportional to both the number of positions of the tibia articular point 74 that are measured along the trajectory 88 and the number of points in the region 72 each of these points is compared with. Generally, the more points used the greater the accuracy of the answer. Natural physical limits on the ability of the cameras to accurately measure small differences in position, as well as the accumulation of numerical errors within the mathematical algorithms used by the software will of course limit the accuracy of the answer.

The method of determining the articular point of a joint according to the invention provides a fast procedure for acquiring accurate preoperative information respecting the position of a joint center which does not require surgery and, thus, enables the surgeon to avoid inflicting unnecessary trauma on a patient.

What is claimed is:

1. A method of obtaining preoperative information determining the position of an articular point of a knee joint between a femur and a tibia of a leg for guiding orthopaedic surgery on the knee joint, the knee joint comprising a patella and medial and lateral epicondyles, the knee joint being located between a hip joint and an ankle joint, the hip joint and the ankle joint located at respective ends of said femur and said tibia, said method comprising the steps of:

fixing a first marker to a portion of said leg comprising said femur;

fixing a second marker to a portion of said leg comprising said tibia;

identifying the positions of said first and second markers in space using a measuring device;

palpating said patella using a third marker;

identifying the position of said patella using said measuring device to measure the position of said third marker in space during said patella palpating step;

determining the position of a femur articular point using a data processing system comprising a microprocessor adapted to receive signals corresponding to positional data of the markers from the measuring device;

defining mathematically a femoral axis extending between said femur articular point and said patella using said data processing system;

palpating said medial and lateral epicondyles using said third marker;

identifying the positions of said epicondyles using said measuring device to measure the position of said third marker in space during said epicondyle palpating step;

defining mathematically, using said data processing system, a plane substantially perpendicular to said femoral axis and at substantially equal respective rectangular distances to the positions of said medial and lateral epicondyles, the intersection of said plane and said femoral axis being an initial estimate of said articular point of said knee joint;

defining a region in said plane having a predetermined size, said region including said initial estimate of said articular point of said knee joint;

determining the position of an articular point of said tibia at said ankle joint;

moving said tibia articular point relatively to said femur by rotating said tibia about said knee joint;

identifying a multiplicity of different positions of said tibia articular point using said measuring device to measure the positions of said first and second markers during said motion of said tibia articular point;

determining mathematically, using said data processing system, one point among a multiplicity of points within said region for which the position is substantially invariant for each of said positions of said tibia articular point, said one point being said articular point of said knee joint; and using the position of said articular point of said knee joint to guide an orthopaedic surgical procedure.

2. A method according to claim 1, wherein said step of determining the position of said femur articular point comprises the steps of:

moving said patella by rotating said femur about said hip joint;

identifying a plurality of positions of said patella during the motion of said patella about said hip joint; and determining mathematically a common point at said hip joint having substantially the same distance to all of said positions of said patella, said common point being said femur articular point.

3. A method according to claim 1, wherein said step of determining the position of an articular point of said tibia at said ankle joint comprises the steps of:

palpating medial and lateral malleoli of said ankle joint with said third marker;

identifying the respective positions of said malleoli using said measuring device to measure the position of said third marker in space during said palpating of said malleoli;

palpating an anterior point of said ankle in the sagittal plane of said tibia with said third marker;

identifying the position of said anterior point using said measuring device to measure the position of said third marker in space during said palpating of said anterior point;

defining mathematically, using said data processing system, a first line between said medial and lateral malleoli, and projecting mathematically, using said data processing system, a second line from said anterior point to intersect said first line at an intersection point, said second line being substantially perpendicular to said first line, said intersection point being said tibia articular point.

4. A method according to claim 1, wherein said substantially invariant point is defined by a point within said region having the smallest standard deviation of distance between said point and said tibia articular point for all of said positions of said tibia articular point.

* * * * *